United States Patent [19]

Grade et al.

[11] Patent Number: 4,462,820
[45] Date of Patent: Jul. 31, 1984

[54] METHOD OF CONTROLLING HARMFUL ORGANISMS USING MONO- AND DIBROMODICYANOMETHANE AND COMPOSITIONS CONTAINING THESE COMPOUNDS FOR THE CONTROL OF SUCH ORGANISMS

[75] Inventors: Reinhardt Grade; Joachim Lorenz, both of Bensheim, Fed. Rep. of Germany

[73] Assignee: Ciba-Geigy Corporation, Ardsley, N.Y.

[21] Appl. No.: 438,221

[22] Filed: Nov. 1, 1982

[30] Foreign Application Priority Data

Nov. 6, 1981 [CH] Switzerland ............. 7111/81

[51] Int. Cl.³ ............. A01N 37/34; C10L 1/22; C10M 1/06; D21D 3/00
[52] U.S. Cl. ............. 71/67; 8/662; 44/72; 44/79; 106/210; 106/288 R; 162/161; 210/764; 252/49.3; 252/49.6; 424/304
[58] Field of Search ............. 424/304; 8/662; 44/72, 44/79; 106/210, 288 R; 162/161; 210/764; 252/49.3, 49.6; 71/67

[56] References Cited

U.S. PATENT DOCUMENTS

| | | | |
|---|---|---|---|
| 2,359,266 | 9/1944 | Hechenbleikner | 424/304 |
| 3,608,084 | 9/1971 | Matt | 424/304 |
| 3,877,922 | 4/1975 | Grier et al. | 424/304 |
| 4,070,400 | 1/1978 | Dybas et al. | 424/266 |

FOREIGN PATENT DOCUMENTS

| | | |
|---|---|---|
| 2247369 | 4/1974 | Fed. Rep. of Germany . |
| 1103391 | 2/1968 | United Kingdom . |

OTHER PUBLICATIONS

Van Haverbeke et al., CA vol. 78 (1973) 153427e.
A. Simek et al., Folia Microbiologica, 14, 508 (1969).
H. J. Hueck et al., Applied Microbiology, 14, 308 (1966).
A. T. Fuller, Biochemical J., 36, 548 (1942).
H. D. Held, Kühlwasser, Vulcan Verlag, 1977, pp. 312-334.
CA, 39, 1708$^9$ (1945).
CA, 81, 13096h (1974).

*Primary Examiner*—Allen J. Robinson
*Attorney, Agent, or Firm*—Luther A. R. Hall

[57] ABSTRACT

A method of using mono- or dibromodicyanomethane for controlling harmful organisms in water, in aqueous systems, in oil or in fuels is disclosed. The compounds act extremely rapidly in very low concentrations.

5 Claims, No Drawings

METHOD OF CONTROLLING HARMFUL ORGANISMS USING MONO- AND DIBROMODICYANOMETHANE AND COMPOSITIONS CONTAINING THESE COMPOUNDS FOR THE CONTROL OF SUCH ORGANISMS

The present invention relates to the control of harmful organisms in water and in aqueous systems or in oils or fuels, using mono- or dibromodicyanomethane as active ingredient.

Halocyanoacetyl derivatives are disclosed as broad spectrum pesticides in British patent specification No. 1 103 391. Dichloromalonitrile is disclosed as insecticide in U.S. Pat. No. 2,359,266. The analogous dibromo compound is known from Beilstein E II 2.539 as an oil which is insoluble in water but volatile in steam.

The present invention relates to the use of mono- or dibromodicyanomethane for controlling harmful organisms in water, in aqueous systems, in oils or in fuels.

Mono- and dibromodicyanomethane are active in exceedingly low concentrations and may be used preferably in concentrations of 1 to 100 ppm and, most preferably, of 2 to 30 ppm. The very good solubility of the compounds in inert organic solvents is of particular interest, for it permits the preparation of concentrated solutions, which is very important, especially for their transportation. It is surprising that the known dibromo compound which is volatile in steam exerts its microbiocidal action fully under conditions (e.g. in cooling towers) in which it is discharged. This shows clearly how rapidly the compounds exert their action even in minimum concentrations. Mono- and dibromodicyanomethane for the control of microorganisms are very effective against harmful microorganisms and for preventing slime formation. The use of these compounds in the practice of this invention is in water or aqueous systems, especially in cooling cycles and in other natural and synthetic, technically aqueous substances. Examples of such substances are cutting and drilling oils, paper and cellulose pulps, aqueous disperse dyes, pigment dispersions, agrochemicals, sizes and starch pastes. Mono- and dibromodicyanomethane may also be used for controlling harmful organisms in oils and fuels, e.g. aviation gasoline, and also in secondary oil recovery.

The present invention also relates to the use of mixtures of mono- and dibromocyanomethane in any ratio.

The method of this invention is normally carried out by applying liquid, pasty or solid formulations. Such formulations may be e.g. suspensions, emulsions and solutions in organic solvents.

Mono- and dibromodicyanomethane may be used by themselves or in formulations or in combination with other biocides, in which connection reference is made especially to the following publications: A. Simek et al. "Antimicrobially active substances", Folia Microbiologica 14, 508-510 (1969); H. J. Hueck et al. "Bacteriostatic fungistatic and algistatic activity of fatty nitrogen compounds", Appl. Microbiology 14, 308-319 (1966); A. T. Fuller "Antibacterial action and chemical constitution in long chain aliphatic bases", Biochem. J. 36, 548-558 (1942) and also H. D. Held, "Kühlwasser" p. 312, Vulkan-Verlag Essen (1977), as well as German Offenlegungsschrift No. 2 247 369 and U.S. Pat. No. 4,070,400.

If the compounds are used in combination with other biocides, these latter are preferably quaternary ammonium or phosphonium compounds, amines, isothiazolone derivatives, chlorophenols, organotin compounds, s-triazines, compounds which split off formaldehyde or sulfur-containing biocides.

Particularly interesting combinations are those preferably with compounds which are not volatile in steam, especially if these compounds have in particular growth inhibiting rather than destructive action.

The following auxiliaries for example may be used for the preparation of the compositions or formulations for controlling harmful organisms: carriers, extenders, emulsifiers, humectants, fixing agents and surfactants. For controlling microorganisms in white water or slime, especially in the paper industry, the formulations may contain detergents and thus remove existing slime or promote the release of the bactericide to destroy existing slime. Examples of carrier materials are: clay, kaolin, talcum, diatomaceous earth, silicic acid, calcium carbonate, benzene, alcohols, esters, xylene, polyols, polyethylene oxide adducts, methyl naphthalene, dimethyl formamide, diethyl sulfoxide, animal and vegetable oils, as well as fatty acids and esters thereof. It is preferred to use solvents as carriers.

The invention also relates to compositions for controlling microorganisms, which compositions contain mono- or dibromodicyanomethane and a conventional auxiliary suitable for use in compositions for controlling harmful microorganisms, the concentration of dibromodicyanomethane or monobromodicyanomethane, based on the entire composition, being 0.1 to 80% by weight, preferably 0.5 to 20% by weight.

Example 1: Destruction of *Pseudomonas aeruginosa*

The overnight culture (ONC), which is grown in caso-peptone broth, of the bacterium strain *Pseudomonas aeruginosa* ATCC 10145, diluted in saline 1:1000. A 1:100 dilution of this suspension is made in tyrode (final dilution $10^{-5}$) and the culture is incubated for 24 hours at 30° C. on a shaking water bath (+biocide 100 mg/l). Then 5 μl are taken from the samples and dropped onto caso-peptone/agar. After further incubation at 30° C. for 24 hours, a visual assessment of growth is made.

TABLE 1

| Concentration in mg/l | Growth | |
| --- | --- | --- |
| | $Br_2C(CN)_2$ | $BrCH(CN)_2$ |
| 2 | (−) | − |
| 5 | − | − |
| 10 | − | − |
| 30 | − | − |
| 60 | − | − |
| 100 | − | − |
| 0 | + | + |

+ = growth, no inhibition
(−) = 1–10 colonies, weak inhibition
− = no growth, all cells destroyed.

Example 2: Determination of the minimum killing concentration of a mixed culture of bacteria To prepare the mixed culture, a sufficient amount of the ONC's reared in caso-peptone broth of the different bacteria strains 1 *Escherichia coli*
4 *Bacillus cereus* var. myciodes
6 *Staphylococcus aureus*
7 *Pseudomonas aeruginosa*
10 *Enterobacter aerogenes*
13 *Proteus vulgaris* is added to tyrode such that a final dilution of 1:1000 is obtained, and the mixed culture is incubated for 24 hours at 30° C. on a shaking water bath.

Then 5 μl are taken from the samples and dropped onto caso-peptone-agar. After further incubation for 24 hours at 30° C., visual assessment of growth is made.

TABLE II

| Concentration (mg/l) | Growth | |
|---|---|---|
| | Monobromodi-cyanomethane | Dibromodi-cyanomethane |
| 2 | + | + |
| 5 | + | + |
| 10 | — | — |
| 30 | — | — |
| 60 | — | — |
| 100 | — | — |
| control | + | + |

+ = growth, no inhibition
— = no growth, all bacteria killed.

Example 3: Determination of the minimum killing concentration of a mixed bacteria culture, different germ count The test is carried out with the strains described in Example 2. The preparation of the mixed culture is effected such that a final dilution of $10^{-2}$, $10^{-3}$ and $10^{-4}$ in tyrode is obtained. The mixed cultures are incubated for 5 hours at 30° C. on a shaking water bath and then samples are taken to determine inhibition.

TABLE III

| Concentration (mg/l) a.i. | Monobromodi-cyanomethane | | | Dibromodicyano-methane | | |
|---|---|---|---|---|---|---|
| | $10^{-2}$ | $10^{-3}$ | $10^{-4}$ | $10^{-2}$ | $10^{-3}$ | $10^{-4}$ |
| 2 | + | + | (+) | + | (+) | — |
| 5 | + | + | — | + | (+) | — |
| 10 | + | — | — | + | — | — |
| 30 | (+) | — | — | (+) | — | — |

+ = growth, no inhibition
(+) = growth, less than control, >10 colonies
— = no growth, all bacteria killed.

It can be seen from Tables I, II and III that the two compounds have excellent bacterial activity. 5 to 10 ppm of the compounds suffice to kill in 5 and 24 hours respectively the slime-forming bacteria which are so important for the treatment of cooling water. In the same concentration range, the compounds also kill the bacteria present in white water in paper manufacture.

Example 4: Test of acitivity in cooling towers

The cycle in the laboratory under illumination (14 hours of light alternating with 10 hours of darkness) has the following technical data:

| (a) volume | 27 liters |
|---|---|
| (b) evaporation | 320 ml/h |
| (c) elutriation loss | 0.8 l/h |
| (d) fresh water = evaporation + elutriation loss | |
| (e) cooling performance: ΔT = 2° C. from 26° C. to 24° C. | |

A natural bacteria flora had developed in the cooling cycle, which was fed with mains water. This flora was treated with 10 ppm of dibromodicyanomethane and 5 or 10 ppm of monobromodicyanomethane (5% formulation in white spirit). The test was evaluated by determining the germ titre by dilution and taking samples with a spatula directly before and after different times at which the biocide is added.

TABLE IV

| Hours after addition | Germ count/ml | | |
|---|---|---|---|
| | 10 ppm of di-bromodicyano-methane | 10 ppm of mono-bromodicyano-methane | 5 ppm of mono-bromodicyano-methane |
| 0 | $4.5 \times 10^6$ | $1.3 \times 10^7$ | $5.6 \times 10^4$ |
| 1 | | $7.2 \times 10^1$ | $4.5 \times 10^1$ |
| 3 | $2.2 \times 10^2$ | $2.6 \times 10^3$ | $3.4 \times 10^2$ |
| 24 | | $4.3 \times 10^6$ | $6.4 \times 10^5$ |
| 28 | $5.9 \times 10^4$ | | |
| 48 | $1.0 \times 10^6$ | | |

Treatment of the cooling tower with dibromodicyanomethane reduces the germ count by $10^4$ in 3 hours; and 28 hours after treatment only about 1% of the bacteria have grown again.

Using 5 ppm of monobromodicyanomethane, 99.9% of the bacteria in the cooling circulation system can be killed in 1 hour.

Monobromodicyanomethane and dibromodicyanomethane therefore have an excellent action in the model cooling tower, although it was to be expected that the compound would quickly volatalise on account of the high rate of evaporation of the system.

Example 5: Test of effectiveness in circulation systems

The circulation systems situated in the open (natural solar radiation, incidence of dust, atmospheric influences) consisted of:
(a) a plastic tub having a volume of 113 liters and an overflow
(b) a pump (21 l/min at 3 m discharge head)
(c) a cooling tower with Oregon pine (sapwood), Oregon pine (heartwood), oak, spruce, asbestos cement and PVC panels.

The supply of fresh water was adjusted so as to compensate for spray and evaporation losses and the biocides were diluted approximately 1:2 over 24 hours. The circulation systems are infected by the natural incidence of dust and not by systematic inoculation. The circulation system was treated twice weekly with 20 ppm of dibromodicyanomethane (25% formulation in diethylene glycol dimethyl ether) to prevent slime formation and the growth of algae.

The test was evaluated by determining the bacterial count by dilution and taking samples on a spatula directly before the addition of biocide and 3 hours afterwards (for the first 7 days, thereafter only directly before the addition of biocide) as well as by visual observation of the growth on the panels.

TABLE V

| Time | Germ count | Addition |
|---|---|---|
| 0 | $1.8 \times 10^4$ | + |
| 3 h | $1.8 \times 10^1$ | |
| 27 h | $9.8 \times 10^2$ | |
| 3 days | $3.3 \times 10^5$ | + |
| 3 days + 3 h | $9.8 \times 10^2$ | |
| 7 days | $2.7 \times 10^5$ | + |
| 7 days + 3 h | $2.6 \times 10^2$ | |
| 10 days | $1.6 \times 10^5$ | |

It was possible to reduce the germ count sharply after each treatment with 20 ppm of dibromodicyanomethane. No slime formation was observed during the entire period of the test and the growth of algae on the woods was greatly reduced in comparison to controls.

Example 6: Action of monobromodicyanomethane + dibromodicyanomethane against Desulfovibrio Activity against a North Sea strain of Desulfovibrio was tested in API Medium No. 38. 0.1 ml of a 14-day-old culture was added to 10 ml of fresh medium and treated with the biocide at 5, 10, 20 and 50 ppm. After 1 hour at 37° C., 0.1 ml is taken to determine the kill and added to 10 ml of fresh medium. Growth inhibition and kill were assessed visually after incubation for 14 days.

TABLE VI

| Concentration mg/l | Inhibition | | Kill | |
|---|---|---|---|---|
| | $BrCH(CN)_2$ | $Br_2C(CN)_2$ | $BrCH(CN)_2$ | $Br_2C(CN)_2$ |
| 5 | − | − | + | + |
| 10 | − | − | + | + |
| 20 | − | − | + | + |
| 50 | − | − | − | − |
| 0 | + | + | + | + |

+ = growth
− = no growth

Monobromodicyanomethane and dibromodicyanomethane are also very effective against Desulfovibrio strains.

Example 7: Action of dibromodicyanomethane in drilling and cutting oils

Test description

The test was carried out with the following cooling lubricant: A partially synthetic drilling oil having an oil content of less than 60% and containing extreme pressure additives and nonionic emulsifiers. The test apparatus was set up in accordance with E. C. Hill, O. Gibbon, P. Davies, Biocides for Use in Oil Emulsions, Tribology International, June 1976.

The concentrate was diluted with $H_2O$ 1:20 and then the lubricant was inoculated with a bacteria/yeast mixed culture (final dilution 1:1000). The mixed culture used for inoculation consisted of the following strains (1:1:1 etc. ratio of ONC's):

*Escherichia coli*
*Staphylococcus aureus*
*Pseudomonas aeruginosa*
*Enterobacter aerogenes*
*Proteus vulgaris*
*Pseudomonas oleovorans*
*Candida albicans*
*Endomyces geotrichum*

The test is evaluated by taking samples before the weekly inoculation and before the addition of 50 mg/l of dibromodicyanomethane in white spirit (addition 2–3 times per week) and the germ count is determined by diluting and streaking out on caso-peptone-agar. Table VII shows clearly the excellent activity of dibromodicyanomethane in this drilling oil. Despite weekly inoculation of bacteria and yeast, the germ count remains under $10^2$ germs/ml of control: $>10^7$ K/ml.

TABLE VII

| Time (days) | Control (K/ml) | Dibromodicyanomethane (K/ml) |
|---|---|---|
| 3 | $10^7$ | 10 |
| 5 | | 10 |
| 7 | $>10^7$ | 30 |
| 10 | | 30 |
| 12 | | 30 |
| 14 | $>10^7$ | 30 |
| 17 | | 10 |
| 19 | | <10 |
| 22 | $>10^7$ | <10 |
| 26 | | 10 |
| 28 | $>10^7$ | <10 |
| 31 | | 20 |
| 33 | | 20 |
| 35 | $>10^7$ | 30 |
| 38 | | 30 |
| 40 | | 40 |
| 42 | $>10^7$ | 40 |
| 45 | | 60 |
| 47 | | 60 |
| 49 | $>10^7$ | 80 |

What is claimed is:

1. A method of inhibiting the growth and reproduction of harmful microorganisms in aqueous systems, in oils or in fuels which comprises contacting said microorganisms with a microbiocidal amount of 1 to 100 parts per million parts of said system, oil or fuel, of monobromodicyanomethane or dibromodicyanomethane.

2. A method according to claim 1, wherein mono- or dibromodicyanomethane is used in a concentration of 2 to 30 ppm.

3. A method according to claim 1, wherein harmful microorganisms are controlled in cooling circulation systems, cutting and drilling oils, paper and cellulose pulps, aqueous disperse dyes, pigment dispersions, agrochemicals, sizes and starch pastes, or in secondary oil recovery.

4. A method according to claim 1, wherein harmful microorganisms are controlled in oils and fuels.

5. A method according to claim 1, wherein harmful microorganisms are controlled in cooling circulation systems.

* * * * *